(12) United States Patent
Safai et al.

(10) Patent No.: US 10,564,111 B2
(45) Date of Patent: Feb. 18, 2020

(54) BORESCOPE FOR GENERATING AN IMAGE WITH ADJUSTABLE DEPTH OF FIELD AND ASSOCIATED INSPECTION SYSTEM AND METHOD

(71) Applicant: The Boeing Company, Chicago, IL (US)

(72) Inventors: Morteza Safai, Newcastle, WA (US); Gary E. Georgeson, Tacoma, WA (US)

(73) Assignee: The Boeing Company, Chicago, IL (US)

( * ) Notice: Subject to any disclaimer, the term of this patent is extended or adjusted under 35 U.S.C. 154(b) by 209 days.

(21) Appl. No.: 15/684,202

(22) Filed: Aug. 23, 2017

(65) Prior Publication Data
US 2019/0064079 A1 Feb. 28, 2019

(51) Int. Cl.
| | | |
|---|---|---|
| G01N 21/954 | (2006.01) | |
| G02B 23/24 | (2006.01) | |
| G02B 3/00 | (2006.01) | |
| G02B 27/00 | (2006.01) | |
| H04N 7/18 | (2006.01) | |

(52) U.S. Cl.
CPC .......... *G01N 21/954* (2013.01); *G02B 3/0056* (2013.01); *G02B 23/2407* (2013.01); *G02B 23/2484* (2013.01); *G02B 27/0075* (2013.01); *G01N 2021/9544* (2013.01); *H04N 7/183* (2013.01)

(58) Field of Classification Search
CPC ......... G01N 21/954; G01N 2021/9544; G02B 23/2407; G02B 23/2484; G02B 3/0056; G02B 27/0075; H04N 7/183
See application file for complete search history.

(56) References Cited

U.S. PATENT DOCUMENTS

| | | | | |
|---|---|---|---|---|
| 6,814,699 B2* | 11/2004 | Ross | ................... | A61B 1/0607 362/555 |
| 8,396,535 B2* | 3/2013 | Wang | ................. | A61B 1/00048 385/12 |
| 2004/0183900 A1* | 9/2004 | Karpen | .............. | G01N 21/8803 348/92 |

(Continued)

OTHER PUBLICATIONS

Hanh N. D. Le, et al., "Experimental assessment of a 3-D plenoptic endoscopic imaging system", Chinese Optics Letters, May 10, 2017, col. 15(5), 051701. (Year: 2017).*

(Continued)

*Primary Examiner* — Brenda C Bernardi
(74) *Attorney, Agent, or Firm* — Kunzler Bean & Adamson (57) ABSTRACT

Defined herein is a borescope, including a tube and a tip. The tube includes a first end and a second end, opposite the first end. The tip is fixed to the first end of the tube and comprises a housing and an image acquisition system. The image acquisition system is within the housing and comprises a light emitting diode ring, a micro-lens array, a main lens, and a photodetector array. The light emitting diode ring includes a plurality of light emitting diodes. The micro-lens array includes a plurality of micro-lenses. The main lens is between the light emitting diode ring and the micro-lens array. The photodetector array includes a plurality of photodetectors. The micro-lens array is between the main lens and the photodetector array.

20 Claims, 6 Drawing Sheets

(56) References Cited

U.S. PATENT DOCUMENTS

| | | | |
|---|---|---|---|
| 2013/0114879 A1* | 5/2013 | Scheid | G06T 7/001 382/145 |
| 2016/0088999 A1* | 3/2016 | Langell | A61B 1/00006 348/68 |
| 2016/0099284 A1* | 4/2016 | Kubala | B26F 1/38 438/68 |
| 2016/0106303 A1* | 4/2016 | Birnkrant | A61B 1/00188 600/109 |
| 2017/0099479 A1* | 4/2017 | Browd | G06F 3/011 |
| 2017/0307439 A1* | 10/2017 | Caucci | G01J 1/4228 |
| 2018/0035053 A1* | 2/2018 | Mak | G03B 9/02 |
| 2018/0063387 A1* | 3/2018 | Wei | H04N 5/2253 |
| 2019/0004305 A1* | 1/2019 | Duckett, III | G02B 23/04 |
| 2019/0049392 A1* | 2/2019 | Ruggiero | G01N 21/954 |

OTHER PUBLICATIONS

Ng et al., Light Field Photography with a Hand-held Plenoptic Camera, Stanford Tech Report CTSR, Feb. 2005, pp. 1-11.

\* cited by examiner

BORESCOPE FOR GENERATING AN IMAGE WITH ADJUSTABLE DEPTH OF FIELD AND ASSOCIATED INSPECTION SYSTEM AND METHOD

FIELD

This disclosure relates generally to non-destructive inspection of a part, and more particularly to non-destructive inspection of a part using a borescope.

BACKGROUND

Borescopes are used to acquire images of difficult-to-access features within a part. Generally, a borescope is an elongate tubular tool equipped with a camera, which is inserted into the part to take pictures of the features from within the part. Conventional borescopes take pictures with a single or limited depth of field. Accordingly, any photographed features outside the depth of field are not in focus. Out-of-focus features are difficult to inspect for defects and measurements. According to conventional techniques, such out-of-focus features are brought into focus only by manipulating the borescope into a different position and taking another picture, which is a tedious and time-consuming exercise. Moreover, these and other shortcomings of conventional borescopes make automated inspection of acquired images for defects and measurements impractical.

SUMMARY

The subject matter of the present application has been developed in response to the present state of the art, and in particular, in response to shortcomings of conventional borescopes used to acquire images of difficult-to-access features within a part. Accordingly, the subject matter of the present application provides a borescope, and associated systems and methods, that overcomes at least some of the above-discussed shortcomings of conventional borescopes. More particularly, in some embodiments, described herein is a borescope that is configured to acquire an image, of a difficult-to-access feature, with an adjustable depth of field for facilitating easier and/or automated inspection of the feature in the image.

Defined herein is a borescope, comprising a tube and a tip. The tube comprises a first end and a second end, opposite the first end. The tip is fixed to the first end of the tube and comprises a housing and an image acquisition system. The image acquisition system is within the housing and comprises a light emitting diode ring, a micro-lens array, a main lens, and a photodetector array. The light emitting diode ring comprises a plurality of light emitting diodes. The micro-lens array comprises a plurality of micro-lenses. The main lens is between the light emitting diode ring and the micro-lens array. The photodetector array comprises a plurality of photodetectors. The micro-lens array is between the main lens and the photodetector array. The preceding subject matter of this paragraph characterizes example 1 of the present disclosure.

The plurality of light emitting diodes are arranged in an annular pattern. The preceding subject matter of this paragraph characterizes example 2 of the present disclosure, wherein example 2 also includes the subject matter according to example 1, above.

The housing comprises an open end and a closed end, opposite the open end. The light emitting diode ring is at the open end of the housing. The preceding subject matter of this paragraph characterizes example 3 of the present disclosure, wherein example 3 also includes the subject matter according to any one of examples 1-2, above.

The plurality of light emitting diodes are configured to produce a uniform, non-focused, light field. The preceding subject matter of this paragraph characterizes example 4 of the present disclosure, wherein example 4 also includes the subject matter according to any one of examples 1-3, above.

Each micro-lens of the plurality of micro-lenses is focused on the main lens. The preceding subject matter of this paragraph characterizes example 5 of the present disclosure, wherein example 5 also includes the subject matter according to any one of examples 1-4, above.

A maximum dimension of the housing, along a plane perpendicular to a central axis of the housing, is between 0.125 inches (3.175 mm) and 0.250 inches (6.35 mm). The preceding subject matter of this paragraph characterizes example 6 of the present disclosure, wherein example 6 also includes the subject matter according to any one of examples 1-5, above.

The borescope further comprises an image transfer circuit, within the housing and electrically coupled to the photodetector array. Moreover, the borescope additionally comprises an electrical communication line, electrically coupled to the image transfer circuit and passing through the tube from the first end to the second end of the tube. The preceding subject matter of this paragraph characterizes example 7 of the present disclosure, wherein example 7 also includes the subject matter according to any one of examples 1-6, above.

The micro-lens array has a pitch of between about 5 microns and about 20 microns. The preceding subject matter of this paragraph characterizes example 8 of the present disclosure, wherein example 8 also includes the subject matter according to any one of examples 1-7, above.

The photodetector array has a pitch between about 1.5 microns and about 3 microns. The preceding subject matter of this paragraph characterizes example 9 of the present disclosure, wherein example 9 also includes the subject matter according to any one of examples 1-8, above.

The tube is flexible and longer than the tip. The preceding subject matter of this paragraph characterizes example 10 of the present disclosure, wherein example 10 also includes the subject matter according to any one of examples 1-9, above.

Also disclosed herein is a system for non-destructively inspecting an interior of a part. The system comprises a borescope, which comprises a tube and a tip. The tube comprises a first end and a second end, opposite the first end. The tip is fixed to the first end of the tube and comprises a housing and an image acquisition system. The image acquisition system is within the housing and comprises a light emitting diode ring, comprising a plurality of light emitting diodes. The image acquisition system also comprises a micro-lens array, comprising a plurality of micro-lenses. The image acquisition system further comprises a main lens, between the light emitting diode ring and the micro-lens array. The image acquisition system additionally comprises a photodetector array, comprising a plurality of sets of photodetectors. The micro-lens array is between the main lens and the photodetector array. Each micro-lens of the plurality of micro-lenses of the micro-lens array is configured to direct light from the main lens to a different set of the plurality of sets of photodetectors and each set of the plurality of sets of photodetectors is configured to generate image data corresponding with the light received from the main lens. The system also comprises a memory configured to record the image data generated by each set of the plurality of sets of photodetectors. The system additionally comprises an image construction module, remote from the tip and configured to construct an image based on the image data recorded on the memory. The preceding subject matter of this paragraph characterizes example 11 of the present disclosure.

The main lens corresponds with one of a plurality of depths of field. Each micro-lens of the plurality of micro-lenses corresponds with a respective one of the plurality of different depths of field. The image construction module constructs the image to have a depth of field corresponding with a first depth of field selected from the plurality of depths of field based at least in part on the image data, recorded in the memory, from the set of photodetectors associated with the micro-lens corresponding with the first depth of field. The preceding subject matter of this paragraph characterizes example 12 of the present disclosure, wherein example 12 also includes the subject matter according to example 11, above.

The image construction module is operable to change the depth of field of the image from the first depth of field to a second depth of field selected from the plurality of depths of field based at least in part on the image data, recorded in the memory, from the set of photodetectors associated with the micro-lens corresponding with the second depth of field. The preceding subject matter of this paragraph characterizes example 13 of the present disclosure, wherein example 13 also includes the subject matter according to example 12, above.

The system further comprises an inspection module configured to automatically inspect the image and at least one of detect pre-defined defects in and take measurements of the part. The preceding subject matter of this paragraph characterizes example 14 of the present disclosure, wherein example 14 also includes the subject matter according to any one of examples 11-13, above.

The inspection module is further configured to automatically command the image construction module to change the depth of the field of the image from the first depth of field to the second depth of field. The preceding subject matter of this paragraph characterizes example 15 of the present disclosure, wherein example 15 also includes the subject matter according to example 14, above.

Additionally disclosed herein is a method of non-destructively inspecting an interior of a part. The method comprises inserting a borescope, comprising a main lens, a photodetector array, and a micro-lens array between the main lens and the photodetector array, through an access opening in the part. The method also comprises concurrently acquiring first image data, using a first micro-lens of the micro-lens array, and second image data, using a second micro-lens of the micro-lens array. The first micro-lens is associated with a first depth of field and the second micro-lens is associated with a second depth of field. The method additionally comprises recording the first image data and the second image data on memory. The method further comprises constructing an image of the interior of the part with the first depth of field based on, at least in part, the first image data and the second image data recorded on the memory. The method also comprises reconstructing the image of the interior of the part to have the second depth of field, based on, at least in part, the first image data and the second image data recorded on the memory. The preceding subject matter of this paragraph characterizes example 16 of the present disclosure.

Acquiring the first image data comprises sensing light, passing through the first micro-lens of the micro-lens array, with a first set of photodetectors of the photodetector array. Acquiring the second image data comprises sensing light, passing through the second micro-lens array, with a second set of photodetectors of the photodetector array. The first set of photodetectors is different than the second set of photodetectors. The preceding subject matter of this paragraph characterizes example 17 of the present disclosure, wherein example 17 also includes the subject matter according to example 16, above.

The method further comprises at least one of automatically inspecting the image for defects in the part or automatically measuring at least one feature of the part in the image. The preceding subject matter of this paragraph characterizes example 18 of the present disclosure, wherein example 18 also includes the subject matter according to any one of examples 16-17, above.

Reconstructing the image of the interior of the part to have the second depth of field is executed automatically to at least one of obtain a measurement of a feature of the part in the second depth of field or inspect the feature of the part in the second depth of field for defects. The preceding subject matter of this paragraph characterizes example 19 of the present disclosure, wherein example 19 also includes the subject matter according to any one of examples 16-18, above.

The method also comprises uniformly lighting the interior of the part with a light emitting diode ring of the borescope. The light emitting diode ring comprises a plurality of light emitting diodes arranged in an annular pattern. The preceding subject matter of this paragraph characterizes example 20 of the present disclosure, wherein example 20 also includes the subject matter according to any one of examples 16-19, above.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter, they are not therefore to be considered to be limiting of its scope.

The subject matter will be described and explained with additional specificity and detail through the use of the drawings, in which.

DETAILED DESCRIPTION

Reference throughout this specification to "one embodiment," "an embodiment," or similar language means that a particular feature, structure, or characteristic described in connection with the embodiment is included in at least one embodiment of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the present disclosure, however, absent an express correlation to indicate otherwise, an implementation may be associated with one or more embodiments.

The present disclosure provides a borescope for acquiring images of features with limited access within an interior of a part. The borescope is configured to acquire image data that enables reconstruction of each image at multiple depths of field without repositioning of the borescope. Accordingly, the images acquired by the borescope of the present disclosure can be manipulated, after the images are acquired, such that every feature in each image is effectively in focus. In other words, the depth of field of an acquired digital image can be selectively switched, retroactively, between multiple depths of field to focus on any of various features or portions of features in the image as desired. With all the features in an image in focus, any one or more of the features can be accurately inspected, whether manually or automatically, for defects, geometric measurements, and feature extraction, among other purposes. Moreover, due to the virtually unlimited depth of field of the borescope, the borescope does not need to be reoriented in order to put in focus all features in a given image area. Therefore, significant time and labor is saved compared to prior art borescope inspection techniques.

Figure 1:
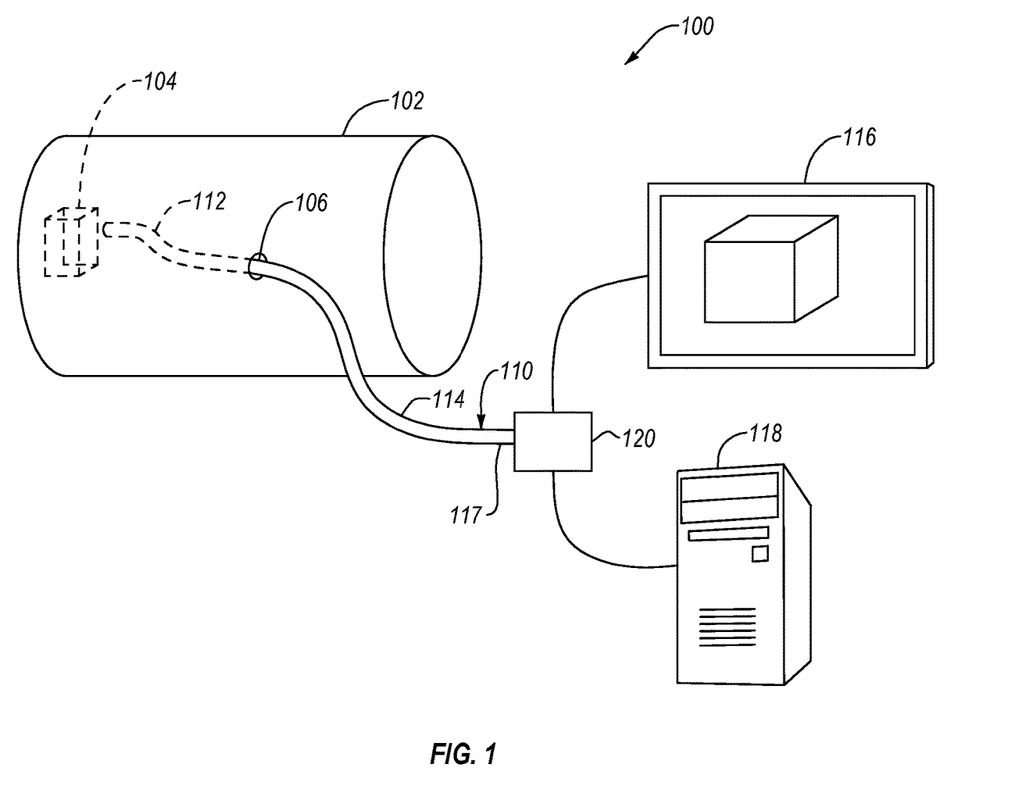
FIG. 1 is a schematic illustration of a system for non-destructively inspecting an interior of a part, according to one or more examples of the present disclosure.

Referring to FIG. 1, according to one embodiment, a system 100 for non-destructively inspecting an interior of a part 102 is shown. The system 100 includes a borescope 110 with a tip 112 that is insertable into an interior of the part 102 via an access opening 106 of the part 102. The position of the tip 112 within the interior of the part 102 can be manipulated to acquire an image of a feature 104 within the interior of the part 102. Generally, the feature 104 can be any of various features of the part 102 with limited access from a location exteriorly of the part 102, such as, for example, internal surfaces of an aircraft, a conduit (e.g., tube, hose, wire) within a vehicle, an internal fastener or beam of a building, blades of a turbine or compressor of a jet engine, and the like. The borescope 110 is used to visually access the feature 104 without destruction or disassembly of the part 102. Often, the borescope 110 gains access to the interior of the part 102 and the feature 104 by entering through an access opening 106. The access opening 106 can be a feature of the part 102. For example, the access opening 102 can be an air intake conduit, exhaust conduit, or vent in an engine, used in operation of the part 102, an aperture designed exclusively for borescope access formed in the part 102 at the time of initial manufacturing of the part 102, or an aperture formed in the part 102 after use of or post-manufacturing of the part 102.

The part 102 can be any of various industrial parts, such as, for example, parts used on aircraft, spacecraft, watercraft, automobiles, robots, and the like. In other implementations, the part 102 can be any of various parts used in other applications, such as, for example, petrochemical, building maintenance, and the like. The application can be medical, in certain implementations, and the part 102 can be an animate object, such as a human being, animal, etc. Alternatively, the system 100 can be used for imagery of difficult-to-reach spaces, which falls under the definition of part as used herein, such as in search-and-rescue applications and industrial security applications (e.g., spying, information retrieval, etc.).

The borescope 110 includes a tube 114 to which the tip 112 is coupled. In one implementation, the tip 112 is non-movably fixed to a first end 115 of the tube 114. However, in another implementation, the tip 112 is movably fixed to the first end 115 of the tube 114, such as via an electromechanical device (e.g., servo motor, solenoid actuator, and the like). Operation of the electromechanical device allows the tip 112 to be moved relative to the tube 114. Such an implementation allows the borescope 110 to acquire different views of the part 102 without moving the tube 114. The tube 114 is hollow to allow a communication line 146 to pass through the tube 114 from the first end 115 at the tip 112 to a second end 117 of the tube 114 opposite the first end 115. In one implementation, the tube 114 is at least partially flexible to facilitate maneuvering of the borescope 110 into and through the interior of the part 102. But, in another implementation, the tube 114 is rigid or non-flexible. The tube 114 can be made from any of various materials, such as polymers and metals. Moreover, the tube 114 is elongate and has any of various lengths sufficient to allow the tip 112 of the borescope 110 to reach and acquire an image of a targeted feature or features within the part 102.

The system 100 further includes a communications router 120 or server in one implementation. The communications router 120 directs data from the borescope 110 to one or more data-using destinations. For example, as shown, the communications router 120 directs data from the borescope 110 to a display 116 and a computing device 118. The display 116 is configured to provide an image of the feature 104 optically acquired by the borescope 110. Moreover, the display 116 may show the feature 104 being optically acquired by the borescope 110 substantially in real time such that a technician is able to monitor the image of the feature 104 as the feature 104 is being optically acquired by the borescope 110. The computing device 118 is configured to record the image acquired by the borescope 110. For example, the computing device 118 has a memory and a processor associated with the memory. The image acquired by the borescope 110 can be recorded on the memory and subsequently accessed via operation of the processor. In this manner, a technician can monitor the image of the feature 104 at some future time after being optically acquired by the borescope 110.

If the image accessed from the memory was acquired using a conventional borescope and was not satisfactory (e.g., a feature was out of focus), it would be difficult for the technician to reacquire a satisfactory image with the conventional borescope because the inspection of the part 102 would likely have been concluded and the conventional borescope would likely have been removed from the part 102 at the time of accessing the unsatisfactory image. However, the borescope 110 of the present disclosure is capable of allowing a technician to change the depth of field of (e.g., to place in focus a feature that was originally not in focus in) an image accessed from the memory and acquired using the borescope 110 if the image was not satisfactory.

Figure 2:
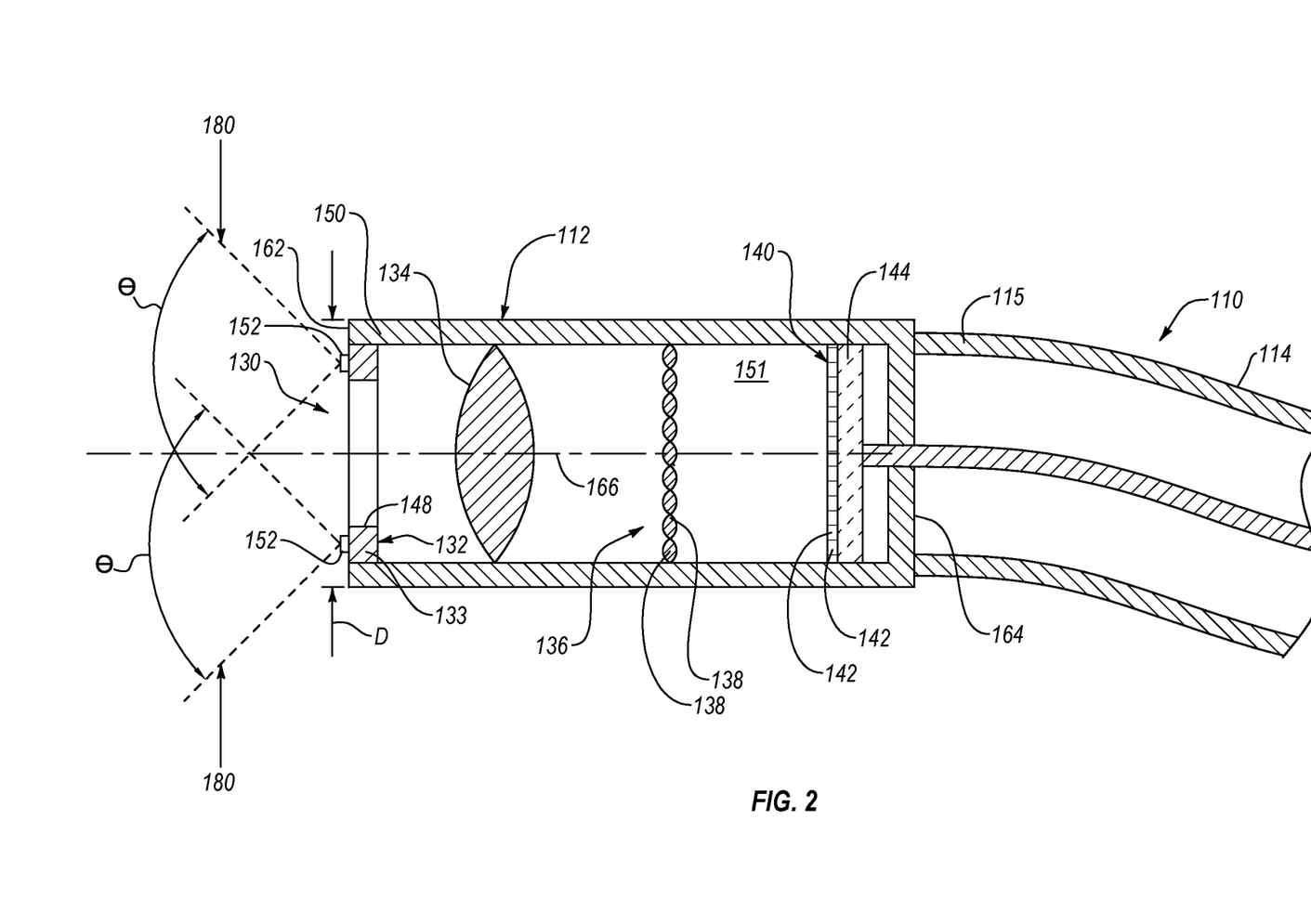
FIG. 2 is an illustration of a cross-sectional side elevation view of a borescope, according to one or more examples of the present disclosure.

Referring to FIG. 2, the tip 112 includes a housing 150 and an image acquisition system 130 within the housing 150. The housing 150 includes an open end 162 and a closed end 164 opposite the open end 162. Moreover, the housing 150 defines a cavity 151 within which the image acquisition system 130 is located. The housing 150, as well as the cavity 151 of the housing 150, has a generally circular cross-sectional shape, along a plane perpendicular to a central axis 166 of the housing 150, in the illustrated implementations. However, in other implementations, the housing 150 and the cavity 151 have cross-sectional shapes, along a plane perpendicular to a central axis 166 of the housing 150, other than circular, such as ovular, triangular, rectangular, polygonal, and the like. According to one implementation, as shown in FIG. 2, a maximum dimension D (e.g., diameter) of the housing 150 is between 0.125 inches (3.175 mm) and 0.250 inches (6.35 mm), which allows the tip 112 of the borescope 110 to access and fit within small spaces that are not accessible by conventional light field cameras. The housing 150 is rigid, or non-flexible, in some implementations. Additionally, the housing 150 is elongate in a lengthwise direction along the central axis 166 of the housing 150. In some implementations, the cross-sectional area of the cavity 151 is constant in the lengthwise direction from the open end 162 to the closed end 164 of the housing 150.

The image acquisition system 130 includes a light emitting diode (LED) ring 132, a main lens 134, a micro-lens array 136, and a photodetector array 140. The LED ring 132 is coupled to the housing 150, at least partially within the cavity 151 of the housing 150, at the open end 162. Alternatively, the LED ring 132 can be attached to the open end 162 of the housing 150 outside of the cavity 151. The LED ring 132 includes a base 133 having an annular or ring-like shape. More specifically, the base 133 fits substantially flush against a surface of the cavity 151 and defines an opening 148 through which light enters the cavity 151 of the housing 150. In some implementations, the opening 148 of the base 133 has a circular shape complementing the circular shape of the cavity 151 of the housing 150 to more uniformly acquire light through the open end 162 of the housing 150.

Figure 3:
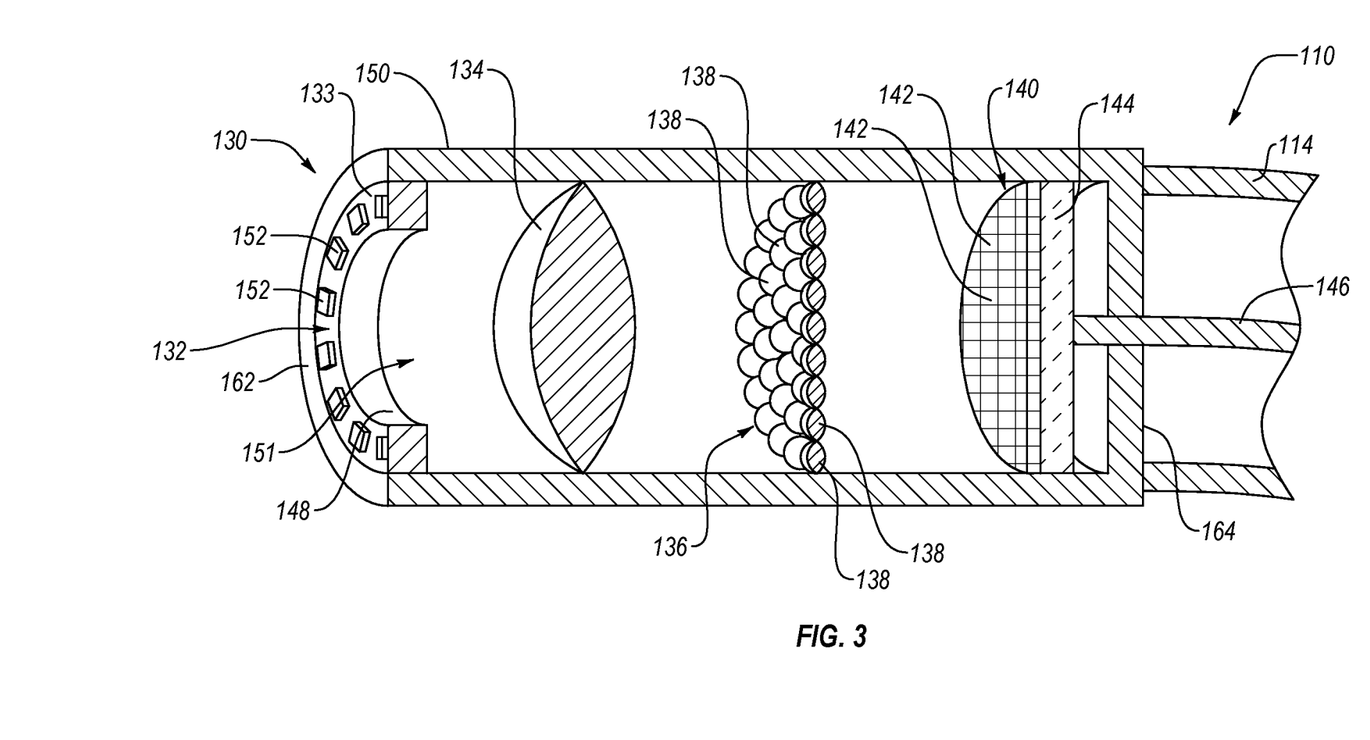
FIG. 3 is an illustration of a cross-sectional perspective view of the borescope of FIG. 2, according to one or more examples of the present disclosure.

Referring to FIG. 3, the base 133 of the LED ring 132 supports a plurality of LEDs 152 or other similar light emitting devices. The plurality of LEDs 152 are coupled to the base 133 circumferentially about the base 133. More specifically, the plurality of LEDs 152 are arranged in an annular pattern about the base 133. The plurality of LEDs 152 are oriented to face outward away from the cavity 151 of the housing 150 in a direction parallel to the central axis 166 of the housing 150. In this manner, the light beam 180 generated by each one of the plurality of LEDs 152 is directed outward away from the cavity 151 of the housing 150. Each one of the plurality of LEDs 152 are configured to generate a light beam 180 with a temperature associated with natural, bright white, or daylight white (e.g., between 3000 kelvin (K) and 10000 K or between 5000 K and 7000 K). Also, each one of the plurality of LEDs 152 has a maximum brightness or intensity between 2000 lumen and 3000 lumen.

Moreover, in some implementations, each one of the plurality of LEDs 152 generates a light beam 180 that is substantially conical-shaped with the central axis of the light beam 180 being parallel with the central axis 166 of the housing 150. Each one of the plurality of LEDs 152 is configured to generate a light beam 180 having a beam angle θ, which is defined as the angle defined between the points on both sides of the spread of the light beam 180 where the intensity of the light beam 180 drops in half. In some implementations, the beam angle θ of the light beam 180 generated by each one of the plurality of LEDs 152 is between 30-degrees and 140-degrees, between 70-degrees and 120-degrees, or at least 90-degrees. According to one implementation, the beam angle θ of the light beam 180 generated by each one of the plurality of LEDs 152 is the same. However, in other implementations, the beam angle θ of the light beam 180 generated by at least two, more than two, or all of the plurality of LEDs 152 is different. Moreover, in some implementations, the radial distance away from the central axis of each one of the plurality of LEDs 152 is the same, while in other implementations, the radial distance away from the central axis of at least two of the plurality of LEDs 152 is different. Each one of the plurality of LEDs 152 is circumferentially spaced apart from at least one adjacent one of the plurality of LEDs 152 by a circumferential distance. The circumferential distances between adjacent ones of the plurality of LEDs 152 is the same in some implementations and different in other implementations.

The configuration (e.g., beam angle θ, temperature, brightness, beam shape, etc.) of the plurality of LEDs 152 and the spatial characteristics (orientation, radial distance, circumferential distance) of the plurality of LEDs 152 are selected to create a uniform, non-focused, daylight, light field within the part 102 and in front of the tip 112 of the borescope. The uniform, non-focused, daylight, light field illuminates features within the part 102 in a manner that promotes acquisition of images of the features with virtually unlimited depths of field by the image acquisition system 130 of the borescope 110. More specifically, such a light field allows accurate and automated defect detection, measurement taking, and feature extraction. The uniformity of the light field generated by the plurality of LEDs 152 ensures features within the part 102 are uniformly illuminated across a depth of field. Moreover, the non-focused nature of the light field promotes uniform illumination of features at each of various depths of field, in contrast to focused light field generated by the camera flashes of conventional cameras, which focuses its highest intensity at only one depth of field.

The main lens 134 of the image acquisition system 130 is located within the housing 150 closer to the closed end 164 of the housing 150 than the LED ring 132. Moreover, the main lens 134 is spaced apart from the LED ring 132 along the central axis 166 of the housing 150. The main lens 134 is a single lens that spans the entire cross-section of the cavity 151 of the housing 150. For example, main lens 134 has a substantially disk-like shape with a circular outer periphery complementing the circular shape of the cavity 151 of the housing 150. In one implementation, the main lens 134 is a simple convex lens or singlet lens. The main lens 134 has a fixed focal length associated with one depth of field centered about a first focal plane FP1 (see, e.g., FIG. 4A). The focal length is the distance between the main lens 134 and a first image plane where the light passing through the main lens 134 is focused. Although not shown, the portion of the main lens 134 through which light 160 is allowed to pass can be controlled via an aperture. However, in one implementation, the image acquisition system 130 does not include an aperture, such that all the light 160 from the opening 148 in the LED ring 132 passes through the main lens 134.

Figure 4A:
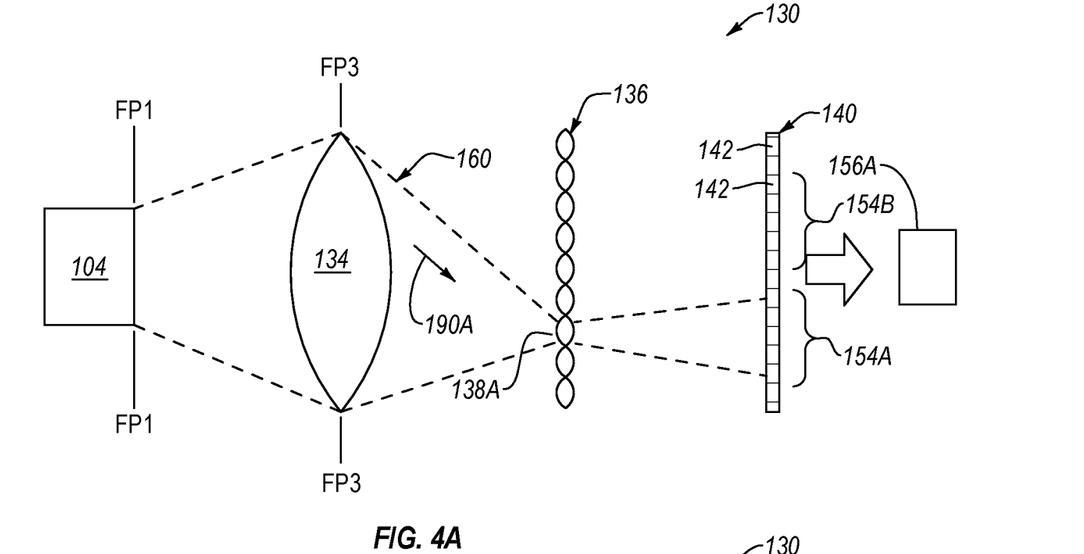
FIG. 4A is a schematic illustration of an optical assembly of a borescope, shown acquiring first image data of a feature, according to one or more examples of the present disclosure.

The micro-lens array 136 is located within the housing 150 closer to the closed end 164 of the housing 150 than the main lens 134. Moreover, the micro-lens array 136 is spaced apart from the main lens 134 along the central axis 166 of the housing 150. More specifically, the micro-lens array 136 is located at the first image plane associated with the main lens 134 such that the light 160 coming through the main lens 134 is focused on the micro-lens array 136. Referring to FIGS. 3 and 4, the micro-lens array 136 includes a plurality of micro-lenses 138 grouped together. Each of the micro-lenses 138 can be a simple convex lens or singlet lens, or other analogous type of lens. At least some of the plurality of micro-lenses 138 are aligned along a plane perpendicular to the central axis 166 and co-planar with the first image plane. The micro-lenses 138 collectively form a substantially disk-like shape with a circular outer periphery complementing the circular shape of the cavity 151 of the housing 150.

Additionally, at least some of the plurality of micro-lenses 138 are arranged such that each of the plurality of micro-lenses 138 abuts an adjacent one, two, three, or four of the plurality of micro-lenses 138. In one implementation, the plurality of micro-lenses 138 are arranged relative to each other such that, for a given size of the micro-lenses 138, the number of micro-lenses 138 per unit area on the first image plane is maximized. However, due to the comparatively smaller size of the tip 112 of the borescope 110 (e.g., multiple orders of magnitude smaller in some implementations) compared to conventional light field cameras, the size of the plurality of micro-lenses 138 is comparatively smaller. For example, in some implementations, the micro-lenses 138 are sized such that the micro-lens array 136 has a pitch of between about 5 microns and about 20 microns. Such a pitch of the micro-lens array 136 facilitates the acquisition of high-resolution images at multiple depths of field despite the smaller size of the borescope 110 compared to conventional light field cameras.

Figure 4B:
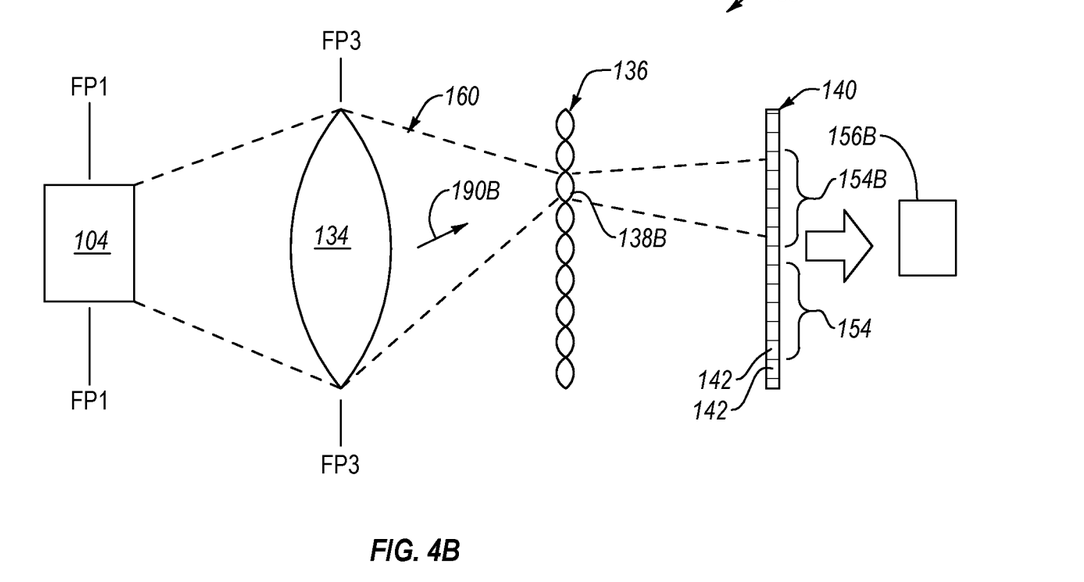
FIG. 4B is a schematic illustration of the optical assembly of FIG. 4A, shown acquiring second image data of the feature, according to one or more examples of the present disclosure.

Each one of the plurality of micro-lenses 138 has a fixed focal length associated with a depth of field at a third focal plane FP3 (see, e.g., FIGS. 4A and 4B). The focal length of the plurality of micro-lenses 138 is the distance between the plurality of micro-lenses 138 and a second image plane where the light passing through the plurality of micro-lenses 138 is focused. As shown, the main lens 134 is located at the third focal plane FP3. Accordingly, each one of the plurality of micro-lenses 138 is configured to focus on the main lens 134. Moreover, each one of the plurality of micro-lenses 138 is located at a different position (e.g., different angle relative to central axis 166 and a central axis of the main lens 134) relative to the main lens 134. Therefore, each one of the plurality of micro-lenses 138 is configured to receive light 160 from the main lens 134 at a different direction than the other ones of the plurality of micro-lenses 138.

For example, as shown in FIG. 4A, a first micro-lens 138A of the plurality of micro-lenses 138 receives light 160 coming from the main lens 134 in a first direction 190A. In contrast, as shown in FIG. 4B, a second micro-lens 138B of the plurality of micro-lenses 138 receives light 160 coming from the main lens 134 in a second direction 190B. Because the plurality of micro-lenses 138 receive light from the main lens 134 at different directions, each one of the plurality of micro-lenses 138 is associated with a different depth of field of the feature 104. More specifically, each one of the plurality of micro-lenses 138 is effectively focused on a different portion of the feature 104 via the reception of light from the feature 104 at different directions. For example, the first micro-lens 138A of the plurality of micro-lenses 138 is effectively focused on a portion of the feature 104 aligned with the first focal plane FP1. In contrast, the second micro-lens 138B of the plurality of micro-lenses 138 is effectively focused on a portion of the feature 104 aligned with the second focal plane FP2.

The photodetector array 140 is located within the housing 150 closer to the closed end 164 of the housing 150 than the micro-lens array 136. More specifically, the photodetector array 140 is located at the second image plane associated with the plurality of micro-lenses 138 of the micro-lens array 136 such that light coming from the plurality of micro-lenses 138 is focused on the photodetector array 140. The photodetector array 140 has a substantially disk-like shape with a circular outer periphery complementing the circular shape of the cavity 151 of the housing 150. Moreover, the photodetector array 140 includes a plurality of photodetectors 142. Each one of the plurality of photodetectors 142 is a sensor configured to detect light and can be any of various photodetectors including semiconductor material formed into p-n junctions that convert light photons into electrical current. However, due to the comparatively smaller size of the tip 112 of the borescope 110 compared to conventional cameras, the size of the plurality of photodetectors 142 is comparatively smaller. For example, in some implementations, the photodetectors 142 are sized such that the photodetector array 140 has a pitch between about 1.5 microns and about 3 microns. In certain implementations, the photodetector array 140 has between about 500,000 and 1,000,000 photodetectors per square inch (i.e., between about 775 and 1,550 photodetectors per square millimeter).

The plurality of photodetectors 142 are effectively divided into a plurality of sets of photodetectors 154 with each set including multiple ones of the plurality of photodetectors 142. The photodetectors of a given set of photodetectors 154 are not shared by or overlap with any other sets of photodetectors 154. Each set of photodetectors 154 corresponds with a respective one of the plurality of micro-lenses 138. More specifically, light passing through each one of the plurality of micro-lenses 138 is sensed only by a respective one of the sets of photodetectors 154. For example, as shown in FIGS. 4A and 4B, light passing through the micro-lens 138A is sensed only by the set of photodetectors 154A and light passing through the micro-lens 138B is sensed only by the set of photodetectors 154B.

The light sensed by each one of the sets of photodetectors 154 is converted into respective image data by an image transfer circuit 144 located within the housing 150 and electrically coupled to the photodetector array 140. For example, referring again to FIGS. 4A and 4B, the light 160 from the micro-lens 138A sensed by the set of photodetectors 154A is converted into first image data 156A and the light 160 from the micro-lens 138B sensed by the set of photodetectors 154B is converted into second image data 156B, which is separate from and different than the first image data 156A. Each image data includes information regarding the color and intensity of the light sensed by the respective one of the sets of photodetectors 154. Additionally, because each set of photodetectors 154 is tied to a particular one of the plurality of micro-lenses 138, which is correspondingly tied to a particular direction of light, each image data includes information regarding the direction of light sensed by the respective one of the sets of photodetectors 154. Generally, the f-number, and overall depth of field, of the image acquisition system 130 is equal to the number of micro-lenses 138 multiplied by a ratio of the focal length of the main lens 134 to the diameter of the main lens 134.

Figure 5:
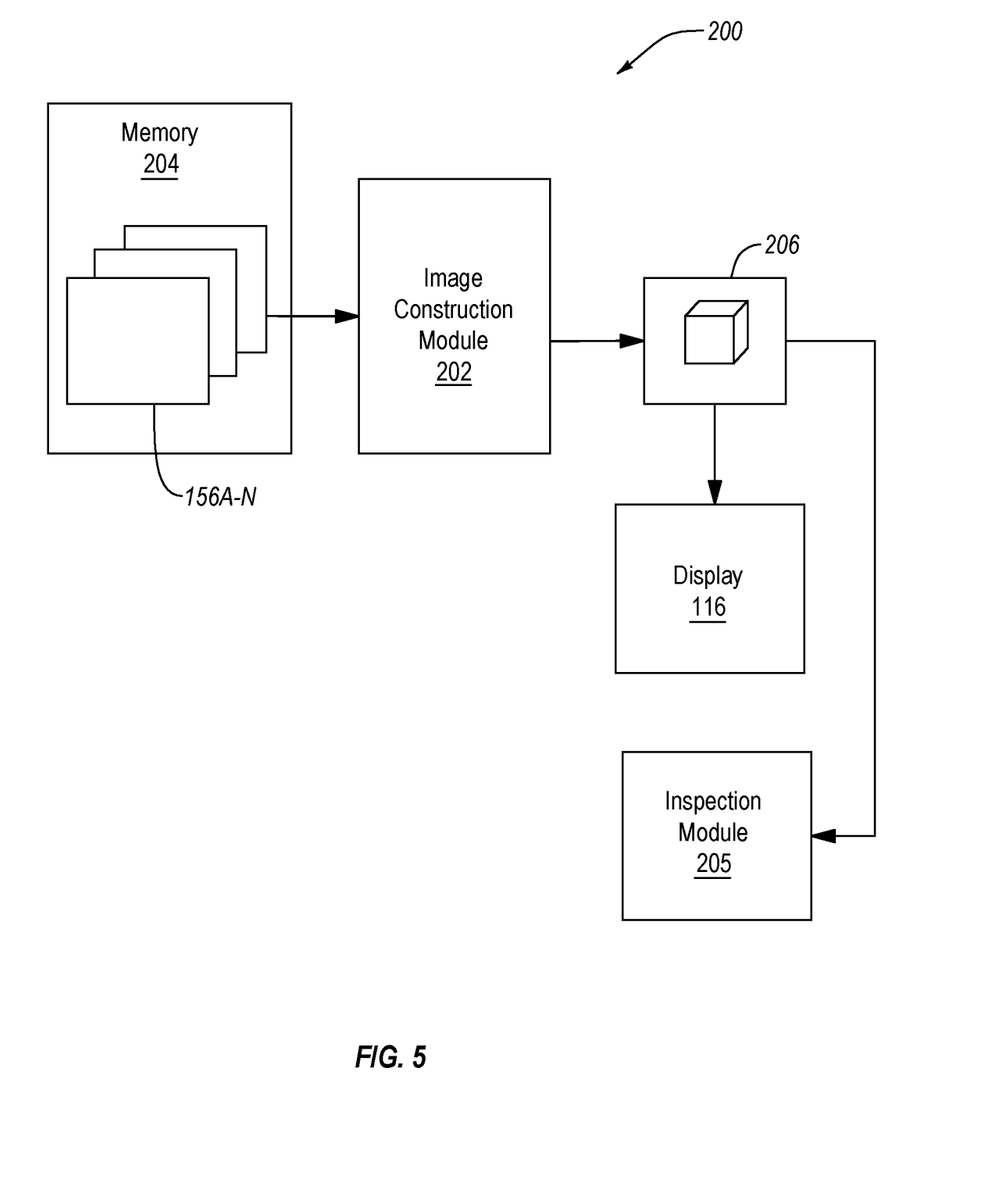
FIG. 5 is a schematic block diagram of a system for non-destructively inspecting an interior of a part, according to one or more examples of the present disclosure.

The image transfer circuit 144 transfers the plurality of image data to a location remote from the tip 112 via the communication line 146. Referring to FIG. 5, according to one embodiment, a system 200 for non-destructively inspecting an interior of a part receives a plurality of image data 156A-N from the image transfer circuit 144. As presented above, each one of the plurality of image data 156A-N was sensed by a respective one of the plurality of sets of photodetectors 154 and includes information regarding the light sensed by the respective one of the plurality of sets of photodetectors 154. The system 200 includes an image construction module 202, which can form part of a computing device, such as the computing device 118. The system 200 further includes a memory 204 that records the plurality of image data 156A-N received from the communication line 146. Accordingly, in one implementation, the image construction module 202 receives the plurality of image data 156A-N from the memory 204, after being recorded on the memory 204. The image construction module 202 is configured to construct an image 206 of the feature 104 based on the plurality of image data 156A-N recorded on the memory 204.

The image construction module 202 can construct the image 206 of the feature 104 based on any of various algorithmic techniques. For example, according to one implementation, the image construction module 202 constructs the image 206 to have a depth of field corresponding with a first depth of field of a plurality of possible depths of field. The first depth of field can be manually selected, such as by via user input from a technician, or automatically selected, such as according to a pre-established routine. The image construction module 202 can construct the image 206 by generating a starting image based primarily on the image data sensed by the set of photodetectors tied to the micro-lens 138 corresponding with the first depth of field. The starting image is then augmented by the image construction module 202, with information from one or more of the other image data sensed by the set of photodetectors tied to other micro-lenses 138 corresponding with the other depths of field, to construct the image 206 with the first depth of field.

In some implementations, it may be desirable to change the depth of field of the image 206 after the image 206 is constructed. For example, to put into focus an otherwise out-of-focus portion of the feature 104, it may be desirable to change the depth of field of the image 206 to place the out-of-focus portion into focus. The image construction module 202 is configured to change the depth of field of the image 206 from one depth of field to another depth of field. For example, where the depth of field is to be changed from the first depth of field to a second depth of field, the image construction module 202 is configured to re-generate a starting image based primarily on the image data sensed by the set of photodetectors tied to the micro-lens 138 corresponding with the second depth of field. The starting image is then augmented by the image construction module 202, with information from one or more of the other image data sensed by the set of photodetectors tied to other micro-lenses 138 corresponding with the other depths of field, to construct the image 206 with the second depth of field. In this manner, the system 200 facilitates the construction and re-construction of an image of a feature 104 to change between multiple depths of field, and thus change the focus of the feature 104 between multiple portions of the feature 104, based on image data acquired at one point in time.

The image 206 constructed by the image construction module 202 is shown on a display 116 for visual inspection by a technician in some implementations. The technician can manually inspect the image 206 for defects, measurements, and the like. Should the technician desire an unfocused portion of the feature 104 in the image 206 to be in focus, so as to provide a more accurate assessment of any defects in the feature 104 or obtain more accurate measurements of the feature 104, the technician can adjust the depth of field of the image 206 via the image construction module 202 to reconstruct the image 206 to place in focus the previously unfocused portion of the feature 104. The reconstructed image 206 can be shown on the display 116 for visually inspection by the technician. In certain implementations, the image construction module 202 includes a graphical user interface, or other user input tool, that allows the technician to quickly and easily select the unfocused portion of the feature 104 to be placed in focus.

According to some implementation, in addition or alternative to manual adjustment of the depth of field of the image 206 by a technician, the depth of field of the image 206 can be adjusted automatically by the image construction module 202 according to a pre-determined routine. For example, the system 200 can further include an inspection module 205 that runs a routine configured to automatically detect defects in the feature 104 in the image 206, measure one or more portions of the feature 104 in the image 206, extract one or more portions of the feature 104, or perform another operation. In one implementation, based on pre-determined preferences, the inspection module 205 automatically digitally scans the portion of the feature 104 that is in focus (e.g., in-focus portion) to detect defects or take measurements of the in-focus portion of the feature 104.

Then, the inspection module 205 automatically commands the image construction module 202 to adjust the depth of field of the image 206, thus re-constructing the image 206, such that at least one out-of-focus portion of the feature 104 is placed in-focus, and scans the newly focused portion of the feature 104 for defect detection or measurements. The inspection module 205 can yet again automatically command the image construction module 202 to adjust the depth of field of the image 206 such that yet another out-of-focus portion of the feature 104 is placed in-focus, and scan the newly focused portion of the feature 104 for defect detection or measurements. The inspection module 205 can automatically command the image construction module 202 to adjust the depth of field of the image 206, and thus change the portion or portions of the feature 104 that is in focus, as many times as needed to obtain a comprehensive and accurate assessment of the defects, measurements, or other characteristics of the feature 104.

Figure 6:
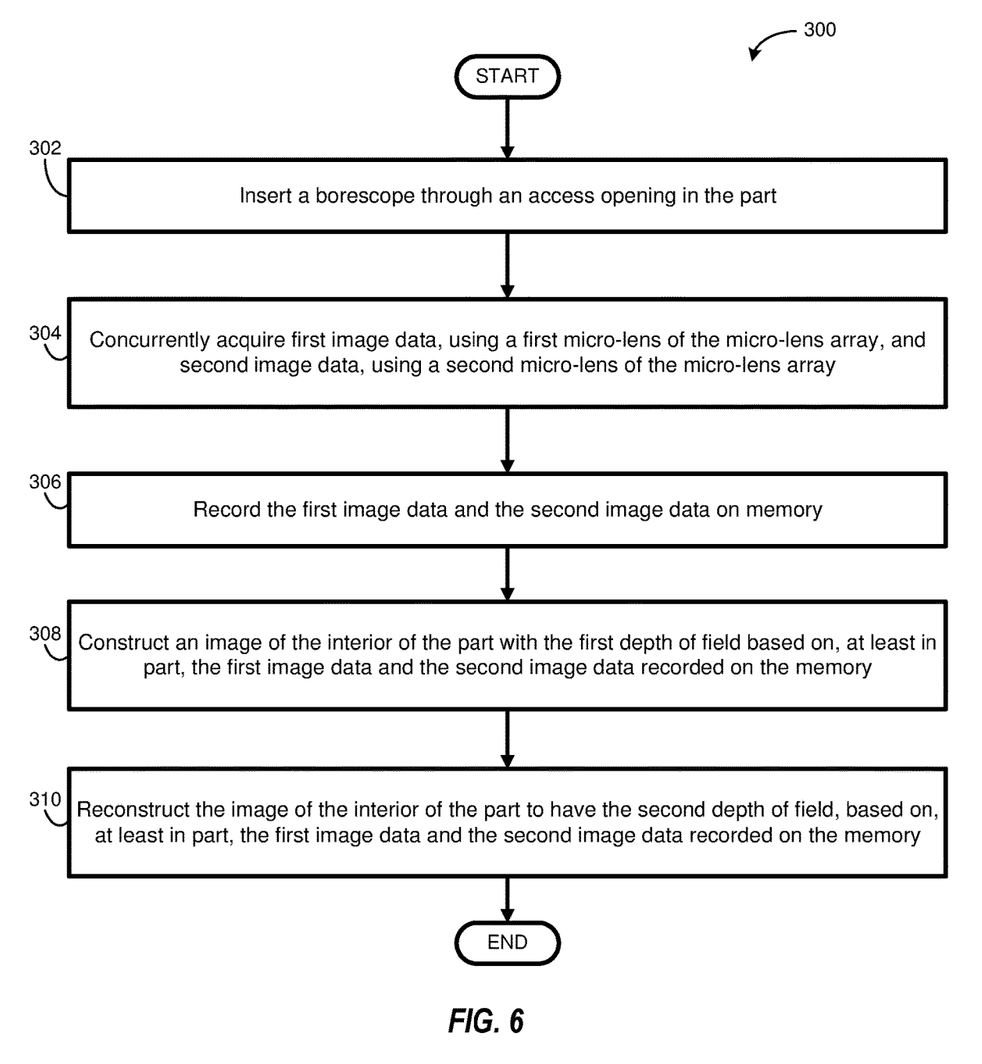
FIG. 6 is a schematic flow diagram of a method of non-destructively inspecting an interior of a part, according to one or more examples of the present disclosure.

According to one embodiment, a method 300 of nondestructively inspecting an interior of a part includes inserting a borescope through an access opening in the part at 302. The borescope includes a main lens, a photodetector array, and a micro-lens array between the main lens and the photodetector array. The method 300 also includes concurrently acquiring first image data, using a first micro-lens of the micro-lens array, and second image data, using a second micro-lens of the micro-lens array at 304. The first micro-lens is associated with a first depth of field and the second micro-lens is associated with a second depth of field. The method 300 additionally includes recording the first image data and the second image data on memory at 306. The method 300 further includes constructing an image of the interior of the part with the first depth of field based on, at least in part, the first image data and the second image data recorded on the memory at 308. The method 300 additionally includes reconstructing the image of the interior of the part to have the second depth of field, based on, at least in part, the first image data and the second image data recorded on the memory at 310. According to some implementations, the method 300 includes the steps performed by any of the various components of the system 100 and/or system 200, and/or technicians operating said components, described above.

In the above description, certain terms may be used such as "up," "down," "upper," "lower," "horizontal," "vertical," "left," "right," "over," "under" and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise. Further, the term "plurality" can be defined as "at least two."

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

As used herein, a system, apparatus, structure, article, element, component, or hardware "configured to" perform a specified function is indeed capable of performing the specified function without any alteration, rather than merely having potential to perform the specified function after further modification. In other words, the system, apparatus, structure, article, element, component, or hardware "configured to" perform a specified function is specifically selected, created, implemented, utilized, programmed, and/or designed for the purpose of performing the specified function. As used herein, "configured to" denotes existing characteristics of a system, apparatus, structure, article, element, component, or hardware which enable the system, apparatus, structure, article, element, component, or hardware to perform the specified function without further modification. For purposes of this disclosure, a system, apparatus, structure, article, element, component, or hardware described as being "configured to" perform a particular function may additionally or alternatively be described as being "adapted to" and/or as being "operative to" perform that function.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Embodiments of the modules of the system 200 may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, embodiments may take the form of a program product embodied in one or more computer readable storage devices storing machine readable code, computer readable code, and/or program code, referred hereafter as code. The storage devices may be tangible, non-transitory, and/or non-transmission. The storage devices may not embody signals. In a certain embodiment, the storage devices only employ signals for accessing code.

The modules of the system 200 may be implemented as a hardware circuit comprising custom VLSI circuits or gate arrays, off-the-shelf semiconductors such as logic chips, transistors, or other discrete components. The modules of the system 200 may also be implemented in programmable hardware devices such as field programmable gate arrays, programmable array logic, programmable logic devices or the like.

The modules of the system 200 may also be implemented in code and/or software for execution by various types of processors. An identified module of code may, for instance, comprise one or more physical or logical blocks of executable code which may, for instance, be organized as an object, procedure, or function. Nevertheless, the executables of an identified module need not be physically located together, but may comprise disparate instructions stored in different locations which, when joined logically together, comprise the module and achieve the stated purpose for the module.

Indeed, a module of code may be a single instruction, or many instructions, and may even be distributed over several different code segments, among different programs, and across several memory devices. Similarly, operational data may be identified and illustrated herein within modules, and may be embodied in any suitable form and organized within any suitable type of data structure. The operational data may be collected as a single data set, or may be distributed over different locations including over different computer readable storage devices. Where a module or portions of a module are implemented in software, the software portions are stored on one or more computer readable storage devices.

Any combination of one or more computer readable medium may be utilized by the modules of the system 200. The computer readable medium may be a computer readable storage medium. The computer readable storage medium may be a storage device storing the code. The storage device may be, for example, but not limited to, an electronic, magnetic, optical, electromagnetic, infrared, holographic, micromechanical, or semiconductor system, apparatus, or device, or any suitable combination of the foregoing.

More specific examples (a non-exhaustive list) of the storage device would include the following: an electrical connection having one or more wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Code for carrying out operations for embodiments may be written in any combination of one or more programming languages including an object oriented programming language such as Python, Ruby, Java, Smalltalk, C++, or the like, and conventional procedural programming languages, such as the "C" programming language, or the like, and/or machine languages such as assembly languages. The code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present subject matter may be embodied in other specific forms without departing from its spirit or essential characteristics. The described embodiments are to be considered in all respects only as illustrative and not restrictive. All changes which come within the meaning and range of equivalency of the claims are to be embraced within their scope.

What is claimed is:

1. A system for non-destructively inspecting an interior of a part, the system comprising:
   a borescope, comprising:
      a tube, comprising a first end and a second end, opposite the first end; and
      a tip, fixed to the first end of the tube and comprising:
         a housing; and
         an image acquisition system, within the housing and comprising:
            a light-emitting-diode ring, comprising a plurality of light-emitting diodes;
            a micro-lens array, comprising a plurality of micro-lenses;
            a main lens, between the light-emitting-diode ring and the micro-lens array; and
            a photodetector array, comprising a plurality of sets of photodetectors, wherein the micro-lens array is between the main lens and the photodetector array;
            wherein each micro-lens of the plurality of micro-lenses of the micro-lens array is configured to direct light from the main lens to a different set of the plurality of sets of photodetectors and each set of the plurality of sets of photodetectors is configured to generate image data corresponding with the light, received from the main lens;
   a memory configured to record the image data generated by each set of the plurality of sets of photodetectors, wherein the image data comprises first image data of a feature of the part and second image data of the feature of the part, the feature of the part comprising at least a first portion and a second portion;
   an image construction module, remote from the tip and configured to:
      construct a first digital image of the feature of the interior of the part based on, at least in part, the first image data and the second image data, and wherein the first portion of the feature is in-focus in the first digital image and the second portion of the feature is out-of-focus in the first digital image; and
      construct a second digital image of the feature of the interior of the part based on, at least in part, the first image data and the second image data, and wherein the second portion of the feature is in-focus in the second digital image and the first portion of the feature is out-of-focus in the second digital image; and
   an inspection module configured to:
      automatically digitally scan only the first portion of the feature in the first digital image to automatically apply a defect-detection routine to the first portion of the feature in the first digital image; and
      automatically digitally scan only the second portion of the feature in the second digital image to automatically apply the defect-detection routine to the second portion of the feature in the second digital image.

2. The system according to claim 1, wherein:
the main lens corresponds with one of a plurality of depths of field;
each micro-lens of the plurality of micro-lenses corresponds with a respective one of a plurality of different depths of field;
a first micro-lens of the plurality of micro-lenses is associated with a first depth of field;
a second micro-lens of the plurality of micro-lenses is associated with a second depth of field;
the first image data is acquired using, in combination, the main lens, the first micro-lens of the plurality of micro-lenses, and the photodetector array; and
the second image data is acquired using, in combination, the main lens, the second micro-lens of the plurality of micro-lenses, and the photodetector array.

3. The system according to claim 1, wherein the defect-detection routine comprises taking measurements of the part.

4. The system according to claim 1, wherein the plurality of light-emitting diodes is arranged in an annular pattern.

5. The system according to claim 1, wherein:
the housing comprises an open end and a closed end, opposite the open end; and
the light-emitting-diode ring is at the open end of the housing.

6. The system according to claim 1, wherein the plurality of light-emitting diodes are configured to produce a uniform, non-focused, light field.

7. The system according to claim 1, wherein each micro-lens of the plurality of micro-lenses is focused on the main lens.

8. The system according to claim 1, wherein a maximum dimension of the housing, along a plane perpendicular to a central axis of the housing, is between 0.125 inches (3.175 mm) and 0.250 inches (6.35 mm).

9. The system according to claim 1, further comprising:
an image transfer circuit, located within the housing and electrically coupled to the photodetector array; and
an electrical communication line, electrically coupled to the image transfer circuit and passing through the tube from the first end to the second end of the tube.

10. The system according to claim 1, wherein the micro-lens array has a pitch of between about 5 microns and about 20 microns.

11. The system according to claim 1, wherein the photodetector array has a pitch between about 1.5 microns and about 3 microns.

12. The system according to claim 1, wherein the tube is flexible and is longer than the tip.

13. The system according to claim 1, wherein:
each one of the plurality of light-emitting diodes generates a light beam, having a beam angle; and
the beam angle is between 70 degrees and 120 degrees.

14. The system according to claim 1, wherein:
each one of the plurality of light-emitting diodes is configured to generate a light beam, having a beam angle; and
a first beam angle of a first light beam, generated by a first one of the plurality of light-emitting diodes, is different than a second beam angle of a second light beam, generated by a second one of the plurality of light emitting diodes.

15. The system according to claim 1, wherein the main lens has a fixed focal length.

16. A method of non-destructively inspecting an interior of a part, the method comprising:
inserting a borescope, comprising a main lens, a photodetector array, and a micro-lens array between the main lens and the photodetector array, through an access opening in the part;
with the borescope fixed relative to a feature of the interior of the part, imaging the feature to concurrently acquire at least first image data using, in combination, the main lens, a first micro-lens of the micro-lens array, and the photodetector array, and second image data, using, in combination, the main lens, a second micro-lens of the micro-lens array, and the photodetector array, and wherein:
the first micro-lens is associated with a first depth of field and the second micro-lens is associated with a second depth of field; and
the feature comprises at least a first portion and a second portion;
digitally recording the first image data and the second image data;
constructing a first digital image of the feature of the interior of the part based on, at least in part, the first image data and the second image data, and wherein the first portion of the feature is in-focus in the first digital image and the second portion of the feature is out-of-focus in the first digital image;
constructing a second digital image of the feature of the interior of the part based on, at least in part, the first image data and the second image data, and wherein the second portion of the feature is in-focus in the second digital image and the first portion of the feature is out-of-focus in the second digital image;
automatically digitally scanning only the first portion of the feature in the first digital image to automatically apply a defect-detection routine to the first portion of the feature in the first digital image; and
automatically digitally scanning only the second portion of the feature in the second digital image to automatically apply the defect-detection routine to the second portion of the feature in the second digital image.

17. The method of claim 16, wherein:
acquiring the first image data comprises sensing light, passing through the first micro-lens of the micro-lens array, with a first set of photodetectors of the photodetector array;
acquiring the second image data comprises sensing light, passing through the second micro-lens, with a second set of photodetectors of the photodetector array; and
the first set of photodetectors is different than the second set of photodetectors.

18. The method of claim 16, wherein the defect-detection routine comprises at least one of:
detecting defects in the part; and
measuring the part.

19. The method of claim 16, wherein reconstructing the first digital image of the feature of the interior of the part and constructing the second digital image of the feature of the interior of the part are executed automatically.

20. The method of claim 16, further comprising uniformly lighting the interior of the part with a light-emitting-diode ring of the borescope, the light-emitting-diode ring comprising a plurality of light-emitting diodes arranged in an annular pattern.

* * * * *